United States Patent [19]

Schulte-elte et al.

[11] Patent Number: 4,543,431
[45] Date of Patent: Sep. 24, 1985

[54] PROCESS FOR THE PREPARATION OF POLYUNSATURATED CYCLOALIPHATIC KETONES

[75] Inventors: Karl H. Schulte-elte, Onex; Roger L. Snowden, Grand-Lancy; Bernard L. Muller, Geneva, all of Switzerland

[73] Assignee: Firmenich SA, Geneva, Switzerland

[21] Appl. No.: 579,946

[22] Filed: Feb. 14, 1984

Related U.S. Application Data

[62] Division of Ser. No. 391,995, Jun. 25, 1982, Pat. No. 4,479,011.

[30] Foreign Application Priority Data

Jul. 23, 1981 [CH] Switzerland ............ 4809/81

[51] Int. Cl.$^4$ ............................................ C07C 33/14
[52] U.S. Cl. ..................................... 568/826; 568/378
[58] Field of Search ............ 568/378, 377, 826

[56] References Cited

U.S. PATENT DOCUMENTS

| 3,890,370 | 6/1975 | Bûchi et al. ............... | 568/377 |
| 3,928,456 | 12/1975 | Kováts et al. ............... | 568/377 |
| 3,956,392 | 5/1976 | de Haan et al. ............... | 568/378 |
| 4,018,718 | 4/1977 | Ochsner et al. ............... | 568/377 |
| 4,172,850 | 10/1979 | Trenkle et al. ............... | 568/378 |
| 4,392,993 | 7/1983 | Thomas et al. ............... | 568/826 |

OTHER PUBLICATIONS

Ohloff et al., Chem. Abst., vol. 90, #4776p (1979).

Primary Examiner—James H. Reamer
Attorney, Agent, or Firm—Pennie & Edmonds

[57] ABSTRACT

Polyunsaturated ketones of formula

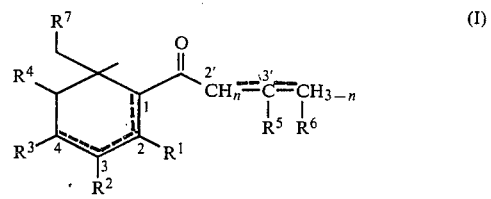

having a double bond in position 2' or 3' of the side chain and possessing either an isolated double bond in position 1 or 2, or two conjugated double bonds in positions 1 and 3 of the ring, as indicated by the dotted lines, and wherein
index n stands for integer 1 or 2, and
each of the symbols $R^1$ to $R^7$, identical or different, designates a hydrogen atom or a lower radical, are prepared by a process which makes use of tertiary diallyl carbinols as starting materials.

1 Claim, No Drawings

PROCESS FOR THE PREPARATION OF POLYUNSATURATED CYCLOALIPHATIC KETONES

This is a division of application Ser. No. 391,995 filed June 25, 1982, now U.S. Pat. No. 4,479,011.

BRIEF SUMMARY OF THE INVENTION

The instant invention relates to a new process for the preparation of polyunsaturated cycloaliphatic ketones of formula

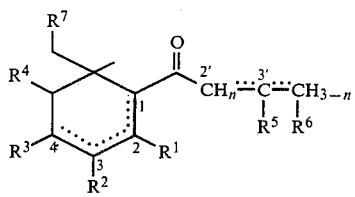

having a double bond in position 2' or 3' of the side chain and possessing either an isolated double bond in position 1 or 2, or two conjugated double bonds in positions 1 and 3 of the ring, as indicated by the dotted lines, and
wherein
index n stands for integer 1 or 2, and
each of the symbols $R^1$ to $R^7$, identical or different, designates a hydrogen atom or a lower alkyl radical, which process consists in treating a diallyl carbinol of formula

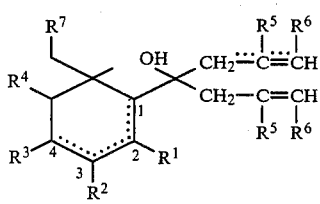

wherein symbols $R^1$ to $R^7$ and the dotted lines have the meaning given above, with a strong base in an inert organic solvent. The invention relates also to 2,5,6,6-tetramethyl-[but-2-en-1-oyl]-cyclohex-2-ene as a new composition of matter of formula (II), as well as to 2,5,6,6-tetramethyl-1-[4-hydroxy-hepta-1,6-dien-4-yl]-cyclohex-2-ene.

The invention relates further to the utilization of 2,5,6,6-tetramethyl-[but-2-en-1-oyl]-cyclohex-2-ene as perfuming and flavoring ingredient.

BACKGROUND OF THE INVENTION

Since their discovery, the cycloaliphatic ketones known as damascones and damascenones, specially $\alpha$- and $\beta$-damascone and $\beta$-damascenone [see E. Demole et al., Helv. Chim. Acta, 53, 541 (1970) and Swiss Pat. No. 520,479], have found an ever increasing utilization in a great variety of applications in both the perfumery and the flavor industry. The interest taken in this class of compounds is shown by the number of scientific publications and letter patents appeared in the last decade and dealing with this subject.

Due to their commercial interest, industry has spent a great deal of efforts in the development of economical industrial processes for their preparation.

PREFERRED EMBODIMENTS OF THE INVENTION

The instant invention relates precisely to a novel practical approach to the synthesis of damascone- and damascenone-like derivatives. Compounds of formula (II), used as starting materials in the process of the invention can be prepared by treating a compound of formula

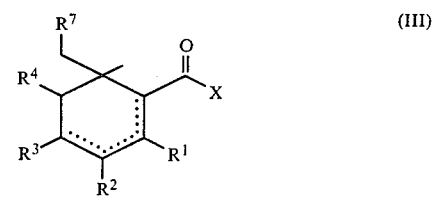

wherein symbols $R^1$ to $R^4$ and $R^7$ as well as dotted lines have the meaning given for formula I, and wherein X represents a radical such as halogen, O—CO-alkyl, O—CO-aryl, O-alkyl, O-aryl or OH, with an organometallic compound having the formula

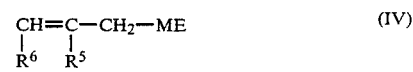

wherein symbol ME designates a metallic function such as Zn, Cd or Mg-halogen. Typically, compounds of formula (III) include ester derivatives of a lower aliphatic alcohol whereas compounds of formula IV are preferably selected among the products resulting from the reaction of allyl-chloride or bromide on magnesium metal.

The reaction is carried out according to the usual techniques commonly employed for the Grignard-type reactions [see: Helv. Chim. Acta, 54, 1767, (1971)]. Compounds (III) can be prepared according to known methods, namely described in Swiss Pat. No. 549,951 or Swiss Pat. No. 563,951, or methods analogous thereto.

The reaction which characterizes the process of the invention consists formally in an anionic splitting promoted by a strong base. To this end, mineral or organic bases such as alkali metal hydrides, alkoxides or hydroxides, preferably sodium or potassium derivatives, are used. Among the said bases one may cite especially sodium or potassium hydride, sodium or potassium tert-butoxide, sodium tert-amylate and sodium methoxide or ethoxide.

The choice among the bases cited above is determined by considerations of economy, safety and occupational health. As a consequence, alkoxides are preferred to hydrides, and among them potassium or sodium tert-butoxide is preferably used.

It could be established that the proportion of the base used must be equal to or higher than the required stoechiometric quantity. In reality, the best yields were achieved by the use of an excess of base.

The reaction times observed are relatively short. To this effect, we should note that the conversion of allylic carbinols into their corresponding damascones or damascenones derivatives (I), according to the instant invention, takes place via the formation of an enolate of formula

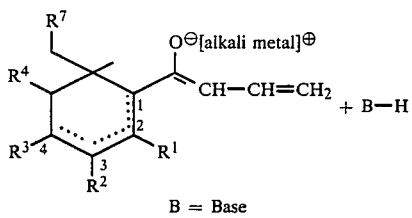

B = Base which compound is unstable in protic media, hence the necessity to stop rapidly the reaction when this is promoted by an alkoxide. Thus at temperatures of between about 20° and 70° C., the reaction times can be of the order of a few minutes when sodium or potassium tert-butylate is the base. When sodium hydride is used instead, the reaction time is longer; for instance, by making use of potassium hydride, 15 hours are necessary to convert 2,6,6-trimethyl-1-[4-hydroxy-hepta-1,6-diene-4-yl]-cyclohex-2-ene to α-damascone in a mixture of tetrahydrofuran and phosphorus hexamethyl-triamide. Of course, temperature exerts a determining influence on reaction times. The process, which in itself is exothermic, can be carried out at a temperature near the room temperature. Values of between about 20° and 70° C. are preferred. At lower temperatures, the reaction times become too long, whereas at temperatures higher than the above given upper limit, we have observed the formation of unwanted by-products.

As described above, the reaction is effected in an inert organic solvent. Suitable solvents include ethers such as tetrahydrofuran or diisopropylether, amides such as dimethylformamide or phosphorus hexamethyl-triamide, an aromatic hydrocarbon, for instance benzene or toluene, an alcohol such as ethyl alcohol or tert-butanol, or even methyl-pyrrolidone or dimethylsulfoxide. Mixtures of the above cited solvents can also be used. According to a preferred embodiment, potassium tert-butoxide is used as base and dimethylformamide or a mixture of dimethylformamide with tetrahydrofuran can be used as a solvent.

The invention is better illustrated by the following examples wherein the temperatures are indicated in degrees centigrade and the abbreviations have the meaning current in the art.

EXAMPLE 1

2,6,6-Trimethyl-[but-3-en-1-oyl]-cyclohex-2-ene(iso-α-damascone) and 2,6,6-trimethyl-[but-2-en-1-oyl]-cyclohex-2-ene(α-damascone)

100 g of 2,6,6-trimethyl-1-[4-hydroxy-hepta-1,6-dien-4-yl]-cyclohex-2-ene have been added at room temperature and under stirring to a solution of 80 g of potassium tert-butoxide in 180 ml of dimethylformamide, while the temperature raised to 60°. After having been left at this temperature for 6 min., the mixture is put into an aqueous HCl solution [150 ml of conc. HCl/200 ml H$_2$O]. A vapour phase distillation has given 4 l of distillate which was then extracted with petrol ether (80°–100°). After the usual treatments of separation, drying and evaporation of the organic extracts, 71 g of a mixture of iso- α-damascone and α-damascone were obtained. Analogous yields were obtained by carrying out the reaction in accordance with the above described method but by replacing aqueous HCl by diluted acetic acid. The complete isomerization of iso- α-damascone into α-damascone can be effected on the obtained mixture by means of an acidic isomerizing agent according to the process described for instance in Swiss Pat. No. 537,352.

EXAMPLE 2

α-Damascone

A mixture of potassium hydride has been prepared by mixing under nitrogen 22 ml of KH, in a 28% dispersion in paraffine (0.132M) in 80 ml of anhydrous tetrahydrofuran (THF) and 20 ml of anhydrous phosphorus hexamethyl-triamide. The mixture was left under stirring for 10 min., then 20 g (0.086M) of 2,6,6-trimethyl-1-[4-hydroxy-hepta-1,6-dien-4-yl]-cyclohex-2-ene were added dropwise thereto within 15 min. The temperature of the mixture was kept below 25° during the addition and thereafter for 16 h, then the mixture was poured onto ice. Upon extraction with ether, separation of the organic extracts and successive washing with a 2N HCL solution, sodium bicarbonate and brine followed by drying over Na$_2$SO$_4$ and evaporation, there was obtained a residue of 46.3 g. This product was diluted with 150 ml of methanol and paraffine was decanted, whereupon the methanolic solution was evaporated to dryness.

The residue was taken up with 100 ml of THF and after addition of 15 ml of 2N HCL was refluxed during 1 h. After extraction with diethyl ether, the organic extracts were subjected to the usual treatments to give 20.4 g of a mixture which upon fractional distillation gave 9.5 g of α-damascone having about 95% purity (yield 55%).

EXAMPLE 3

α-Damascone 4.5 g sodium hydride at 80% in a dispersion of paraffine (0.15M) were mixed to 100 ml of dimethyl sulfoxide and the mixture was heated to 65° under stirring until the hydrogen evolution ceased. The mixture was then cooled to 50° and 23.4 g (0.1M) of 2,6,6-trimethyl-1-[4-hydroxy-hepta-1,6-dien-4-yl]-cyclohex-2-ene were added thereto, whereupon it was left for 3 h under the stirring at this temperature then for one night at room temperature. The mixture was finally poured onto ice and extracted with ether. The combined organic extracts were subjected to the usual treatment of washing, neutralization and drying. By evaporation, there was obtained 27.6 g of a residue which was dissolved in 100 ml of THF. 15 ml of a 2N aqueous HCL solution were added to the obtained solution and the resulting mixture was refluxed for 1 h. After cooling, the reaction mixture was poured onto ice and extracted with ether. The usual treatments gave 11.7 g of α-damascone (yield 61%).

EXAMPLE 4

α-Damascone 23.4 g (0.1M) of 2,6,6-trimethyl-1-[4-hydroxy-hepta-1,6-dien-4-yl]-cyclohex-2-ene have been added under stirring in an atmosphere of nitrogen, to a mixture of 15.5 g (0.15M) of potassium tert-butoxide in 200 ml of dimethylformamide (DMF). The temperature of the mixture had thus increased to about 40°. After having been left under stirring for ½ h, the mixture was poured onto ice, then extracted with ether. The ethereal extracts were acidified with a 2N HCL solution, and successively washed with a saturated aqueous NaHCO$_3$ solution and with water, and finally dried. The evaporation of ether gave 15.3 g of a residue which was taken up with 100 ml of THF. After acidification with 15 ml of a 2N HCl solution, the whole was refluxed for 1 h. The resulting cooled mixture was diluted with ether, washed with a solution of sodium bicarbonate and water until neutrality and finally dried to yield 15 g of a residue which by fractional distillation gave 12 g of α-damascone (yield 62%).

EXAMPLE 5

β-Damascone 2.34 g (0.01M) of 2,6,6-trimethyl-1-[4-hydroxy-hepta-1,6-dien-4-yl]-cyclohex-1-ene were added in a nitrogen atmosphere and under stirring to a suspension of 1.55 g of potassium tert-butoxide (0.015M) in 20 ml of DMF, while the temperature of the mixture raised to 35°. After having been left under stirring during 15 min., the reaction mixture was taken up with ether, washed with a 2N HCL solution and successively with NaHCO₃ and water until neutrality. By evaporation, there was obtained a residue which after having been dissolved in 10 ml of THF, was acidified with 1 ml of 2N HCl and then put to reflux for 1 h.

The resulting mixture was taken up with ether, washed and neutralized to give 2 g of a residue which upon distillation gave 15.5 of β-damascone.

EXAMPLE 6

β-Damascenone 11.6 g (0.05M) of 2,6,6-trimethyl-1-[4-hydroxy-hepta-1,6-dien-4-yl]-cyclohexa-1,3-diene were treated as indicated in the preceding example with 8.6 g (0.075M) of potassium tert-butoxide in 50 ml of DMF. β-Damascenone was obtained in 80% yield (7.1 g).

EXAMPLE 7

2,5,6,6-Tetramethyl-[but-2-en-1-oyl]-cyclohex-2-ene 5.5 g of 2,5,6,6-tetramethyl-1-[4-hydroxy-hepta-1,6-dien-4-yl]-cyclohex-2-ene were treated as indicated in Example 5 with 5.8 g of potassium tert-butoxide in 50 ml of DMF to give 3.5 g of a mixture containing 45% of the desired product under the form of its trans isomer, and 15% of its cis isomer having the following formulae

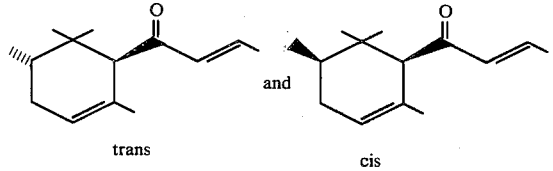

trans          cis

The two isomers can be separated one from the other by vapour phase chromatography.

Their analytical characteristics were the following:
trans:
IR: 3050, 1695, 1645, 1625, 980 and 818 cm⁻¹;
NMR (CDCl₃): 0.80; 0.85; 1.55; 1.88; 2.98; 5.55; 6.3; 6.6–7.02 δ ppm;
MS: M⁺=206(22); m/e: 191(10), 163(1), 149(6), 137(30), 121(10), 109(8), 95(28), 81(12), 69(100), 57(12), 41(28).
cis:
IR: 3045, 1690, 1665, 1625, 980 and 810 cm⁻¹;
NMR (CDCl₃): 0.72; 0.87; 0.96; 1.56; 1.9; 3.18; 5.58; 6.2; 6.6–7.3 δ ppm;
MS: M⁺=206(12); m/e: 191(3), 137(18), 121(5), 109(6), 95(17), 81(5), 69(100), 57(7), 41(18).

These compounds are new. They are characterized by an elegant odor of α-damascone type; the perfuming character of the trans isomer is however finer, more fruity and flowery than that of the corresponding cis isomer. The diallyl carbinol, used as starting material in the described process, was prepared in accordance with the method illustrated by the following reaction scheme:

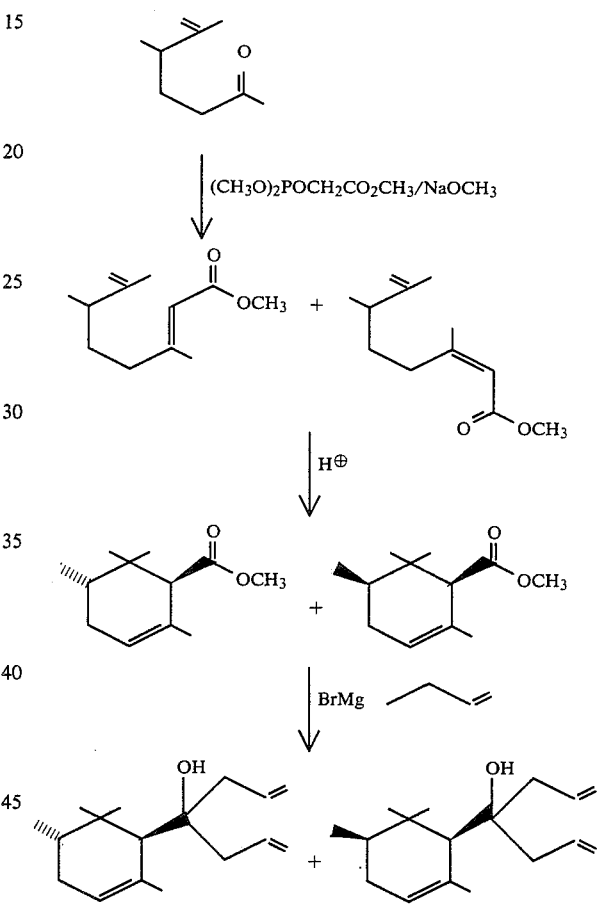

a. 54 g of sodium methoxide were added to a mixture of 42 g of 5,6-dimethyl-hept-6-en-2-one and 60 g of methyl trimethyl-phosphonoacetate in 190 ml of petrol ether (1½ h) under nitrogen and stirring, and the resulting mixture was refluxed for 1½ h. After cooling, dilution with 40 ml of water and extraction with ether, the combined organic extracts were treated as usual to give 56.7 g of a product which, by distillation over a Vigreux column at 0.05 Torr gave, at 41°–42°, 45 g (71%) of a cis-trans isomeric mixture of methyl 2,3,6-trimethyl-octa-1,6-dienoate.

b. 20 g of the mixture of esters obtained under letter a. above were refluxed for 4 h in the presence of 10 g of acidic diatomaceous earth in 100 ml of toluene.

After filtration and distillation, there were obtained 19 g of residue which upon fractional distillation by means of a Vigreux column at 0.1 Torr gave 15 g of a mixture in a weight ratio of ca. 55:30:15 of methyl trans- 2,5,6,6-tetramethyl-cyclohex-2-en-1-carboxylate, its cis isomer and methyl-2,5,6,6-tetramethyl-cyclohex-1-en-1-carboxylate. The two cyclohex-2-enic esters were separated each from the other by preparative gas chromatography.

c. 14.2 g of the mixture thus obtained were treated under a nitrogen atmosphere according to a Grignard-type reaction with 29 g of allyl bromide in 100 ml of anhydrous ether in the presence of 5.8 g of magnesium turnings and some crystals of iodine.

The usual treatments gave 9.5 g of a mixture containing ca. 50% of the desired diallylic carbinol.

IR: 3560, 3085, 1642, 1005, 910 and 820 cm$^{-1}$;

NMR (CDCl$_3$): 0.82; 1.17; 1.82; 2.45; 4.85–6.3; 5.5 δ ppm;

MS: m/e: 206(1), 176(3), 153(13), 135(100), 124(24), 107(48), 93(85), 79(65), 67(48), 55(80), 41(70).

What we claim is:

1. 2,5,6,6-Tetramethyl-1-[4-hydroxy-hepta-1,6-dien-4-yl]-cyclohex-2-ene.

* * * * *